United States Patent [19]

Tamura et al.

[11] Patent Number: 5,225,508

[45] Date of Patent: Jul. 6, 1993

[54] OPTICAL RESIN OBTAINED FROM DIETHYLENICALLY UNSATURATED MONOMER

[75] Inventors: Yutaka Tamura; Fumie Watari, both of Ami, Japan

[73] Assignee: Mitsubishi Petrochemical Company Limited, Tokyo, Japan

[21] Appl. No.: 710,447

[22] Filed: Jun. 5, 1991

Related U.S. Application Data

[62] Division of Ser. No. 599,437, Oct. 18, 1990, abandoned.

[30] Foreign Application Priority Data

Oct. 19, 1989 [JP] Japan .................. 1-272649

[51] Int. Cl.$^5$ .............................. C08F 28/04
[52] U.S. Cl. ......................... 526/289; 359/642; 568/57
[58] Field of Search ......................... 526/289

[56] References Cited

U.S. PATENT DOCUMENTS 2,163,176 6/1939 Keyssner .................. 568/57
2,888,442 5/1959 Uraneck .................. 526/289

OTHER PUBLICATIONS

Chemical Abstract No. 113 (20): 178316x (1990) Kawaki et al.

*Primary Examiner*—Christopher Henderson
*Attorney, Agent, or Firm*—Wegner, Cantor, Mueller & Player

[57] ABSTRACT

Disclosed are a diethylenicallyunsaturated monomer represented by the following formula [Ia]:

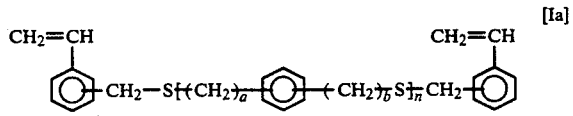

wherein n is an integer of from 1 to 10, and a and b each represent 0 or an integer of from 1 to 4, and an optical resin which is substantially insoluble and infusible and has a refractive index $\eta_D$ of at least 1.62, and which is obtained by polymerizing a monomer comprising 50 to 100% by weight of this diethylenically unsaturated monomer.

7 Claims, No Drawings

OPTICAL RESIN OBTAINED FROM DIETHYLENICALLY UNSATURATED MONOMER

This application is a divisional of Ser. No. 07/599,437, filed Oct. 18, 1990 now abandoned.

BACKGROUND OF THE INVENTION

(1) Field of the Art

The present invention relates to an optical resin having a high refractive index, and a diethylenically unsaturated monomer which gives this optical resin. More particularly, the present invention relates to an optical resin of a light weight, having an excellent heat resistance, an excellent optical uniformity and a good adaptability to cast polymerization molding and also having a high refractive index, and also relates to a diethylenically unsaturated monomer which gives this optical resin.

(2) Description of the Related Art

Recently, highly transparent plastic materials are used as optical articles such as lenses, optical fibers and optical disc substrates instead of inorganic glass materials while utilizing excellent characteristics of these plastic materials such as a light weight, an easy moldability and a high safety.

However, in case of, for example, polymethyl methacrylate or polydiethyleneglycol bisallyl carbonate, the refractive index $\eta_D$ is as low as 1.49 to 1.50, and when the material is used for lenses and the like, requirements of further reduction of the weight and further compaction are not sufficiently satisfied.

In case of, for example, polystyrene and polycarbonate, the refractive index $\eta_D$ is about 1.58 to about 1.59 and is relatively high, but since these materials are thermoplastic resins, the heat resistance is poor and optical strain is readily caused by the birefringence at the molding step. Moreover, these materials are defective in that the solvent resistance and scratch resistance are poor.

Use of a crosslinkable monomer having a high refractive index is recently proposed for providing a material having a high refractive index and overcoming the foregoing defects. For example, use of polyfunctional monomers having an aromatic ring substituted with a halogen atom, such as a tetrabromobisphenol A skeleton (Japanese Unexamined Patent Publication No. 57-147505, Japanese Unexamined Patent Publication No. 58-18602, Japanese Unexamined Patent Publication No. 60-51706, Japanese Unexamined Patent Publication No. 61-64716 and Japanese Unexamined Patent Publication No. 61-28901) and a tetrabromophthalic acid skeleton (Japanese Unexamined Patent Publication No. 60-166307, Japanese Unexamined Patent Publication No. 60-173006 and Japanese Unexamined Patent Publication No. 60-137912), and monomers having a styrene group introduced as the functional group in an alkylene sulfide skeleton (Japanese Unexamined Patent Publication No. 59-164501) as main components or comonomer components has been proposed.

However, most of these polyfunctional monomers having a high refractive index are solid at room temperature, and therefore, cast polymerization molding of these monomers is difficult and a reactive diluent such as styrene is used in combination while admitting that this results in reduction of the refractive index. In case of the monomer having a styrene group introduced in an alkylene sulfide skeleton, if the chain length of the alkylene sulfide skeleton is short, troubles such as cracking at the cast polymerization molding and breaking at the release from a mold are often caused, and the impact resistance is degraded. These defects are due to the fact that the distance between crosslinking sites is unduly short, and these defects are eliminated by increasing the length of the alkylene sulfide skeleton, but this results in reduction of the refractive index. Moreover, the halogen-containing monomer is defective in that the specific gravity is large.

SUMMARY OF THE INVENTION

It is a primary object of the present invention to solve the foregoing problems and provide an optical resin of a light weight, being excellent in heat resistance, optical uniformity and cast polymerization moldability and having a high refractive index.

In accordance with the present invention, there is provided a diethylenically unsaturated monomer represented by the following formula [Ia]:

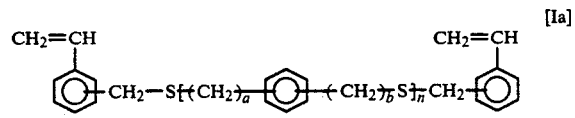

wherein n is an integer of from 1 to 10, and a and b each represent 0 or an integer of from 1 to 4.

Furthermore, in accordance with the present invention, there is provided an optical resin formed by using the above diethylenically unsaturated monomer, which comprises recurring units represented by the following formula [Ib]:

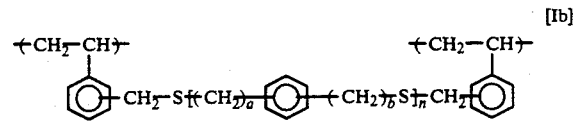

wherein n is an integer of from 1 to 10 and a and b each represent 0 or an integer of from 1 to 4.

The optical resin of the present invention has a light weight, is excellent in heat resistance, optical uniformity and cast polymerization moldability and has a high refractive index of $\eta_D \geq 1.62$.

DETAILED DESCRIPTION OF THE PREFERRED EMBODIMENTS

1. Monomer

The optical resin of the present invention comprises recurring units represented by the above mentioned formula [Ib]. These recurring units can be formed by polymerization of a diethylenically unsaturated monomer represented by the following formula [Ia]:

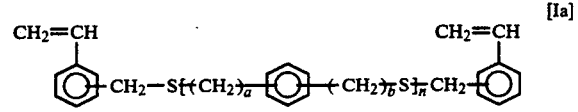

wherein n is an integer of from 1 to 10, and a and b each represent 0 or an integer of from 1 to 4.

It is considered that this diethylenically unsaturated monomer has a structure in which styrene molecules are connected through a thioether chain. The position of the connection of the thioether chain to the styrene moiety may be any of o-, m- and p-positions, but m- and p-positions are typical. In the case where a phenylene group is present in this thioether chain, the substitution position may be any of o-, m- and p-positions, but m- and p-positions are typical.

In above formula [Ia], n is preferably from 1 to 6, and each of a and b is preferably from 0 to 2. It is preferred that a and b should have the same meaning.

Specific examples of the monomer [Ia] in which n is 1 are described below:

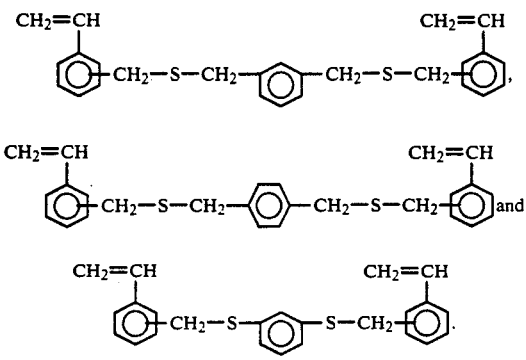

These monomers can be synthesized by reacting chloromethylstyrene (for example, a mixture of m- and p-chloromethylstyrenes) with a desired dimercaptan such as m-xylylene dimercaptan, p-xylylene dimercaptan or m-benzene dithiol in the presence of a base such as sodium hydroxide, potassium hydroxide or potassium carbonate. This reaction is preferably carried out in a solvent. An alcohol, a water-alcohol mixture and a ketone are especially preferably used as the solvent.

Another example of the monomer of formula [Ia] is the following compound:

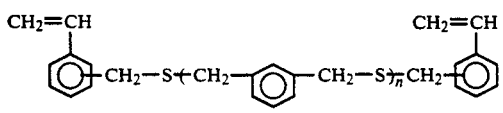

wherein n is an integer of from 1 to 10. The product, however, is practically a mixture of those of various integers n, wherein the n is an average of various n's.

Monomers of this type can be obtained by reacting chloromethylstyrene (for example, a mixture of m-chloromethylstyrene and p-chloromethylstyrene) and m-xylene dichloride with an alkali metal sulfide such as sodium sulfide. Also in this reaction, a solvent such as an alcohol, a water-alcohol mixture or a ketone is preferably used. The n value (average value) of the monomer obtained can be controlled by controlling the ratio among chloromethylstyrene, m-xylylene dichloride and sodium sulfide and preferably n is from more than 1 to 2.5.

2. Polymer

The optical resin of the present invention can be obtained by polymerizing at least one monomer of formula [Ia] or by copolymerizing at least one monomer of formula [Ia] with a monomer copolymerizable therewith, and this optical resin comprises recurring units represented by above formula [Ib].

As the radically polymerizable monomer to be copolymerized, there can be mentioned (a) vinyl compounds such as styrene, vinyltoluene, methoxystyrene, chlorostyrene, bromostyrene, dichlorostyrene, dibromostyrene, divinylbenzene, vinylnaphthalene and vinyl acetate, (b) (meth)acrylic compounds such as methyl methacrylate, phenyl methacrylate, phenyl acrylate, chlorophenyl methacrylate, bromophenyl methacrylate, benzyl methacrylate, 2-hydroxyethyl methacrylate, glycidyl methacrylate, epoxy acrylate, diethyleneglycol dimethacrylate, triethyleneglycol dimethacrylate, 1,6-hexanediol dimethacrylate, a dimethacrylate of an ethylene oxide adduct to bisphenol A, a dimethacrylate of an ethylene oxide adduct to tetrabromobisphenol A and p-bis($\beta$-methacryloyloxyethylthio)xylylene, and (c) allyl compounds such as diethyleneglycol bisallyl carbonate, diallyl phthalate, diallyl epoxysuccinate, allylphenylsilane and diallyldimethylsilane. The copolymerization ratio of the radical polymerizable unsaturated monomer is generally in the range of from 1 to 90% by weight. In view of the purport of the present invention, it is preferred that the monomer of formula [Ia] should comprise at least 50% by weight.

The polymerization is generally carried out according to the radical polymerization process using a radical polymerization initiator. For example, known bulk polymerization, suspension polymerization and emulsion polymerization techniques can be adopted.

The kind of the radical polymerization initiator used for the polymerization is not particularly critical, and ordinary initiators can be used. For example, there can be used peroxides such as benzoyl peroxide, diisopropyl oxycarbonate, tertiary butyl peroxyisopropyl carbonate and di-tertiarybutyl peroxide, and azo compounds such as azobisisobutyronitrile and azobismethylvaleronitrile. The radical polymerization initiator is used in an amount of 0.01 to 10% by weight, preferably 0.1 to 5% by weight, based on the whole monomers. The reaction is preferably carried out at a polymerization temperature of 20° to 120° C. for about 1 to about 72 hours.

The polymerization can also be accomplished by the known photopolymerization technique using an ordinary photopolymerization initiator.

The kind of the photopolymerization initiator used for the polymerization is not particularly critical. Ordinary initiators can be used. For example, there can be used acetophenone-type initiators such as acetophenone, diethoxyacetophenone, 2-hydroxy-2-methyl-1-phenylpropan-1-one and 1-hydroxycyclohexylphenylketone; benzoin-type initiators such as benzoin, benzoin ethyl ether and benzyldimethylketal; benzophenone-type initiators such as benzophenone, methyl benzoylbenzoate and 4-phenylbenzophenone; thioxanthone-type initiators such as thioxanthone, 2-methylthioxanthone and 2,4-diethylthioxanthone; and acylphosphine oxide and benzil. The photopolymerization initiator is used in an amount of 0.01 to 10% by weight, preferably 0.05 to 5% by weight, based on the whole monomers. The reaction is carried out at an irradiation dose of 0.01 to 100 J/cm$^2$, preferably 0.1 to 30 J/cm$^2$.

The polymerization can be accomplished by combining the radical polymerization process and the photopolymerization process.

The present invention will now be described in detail with reference to the following examples that by no means limit the scope of the invention.

EXAMPLE 1

(1) At room temperature, 0.2 mole of chloromethylstyrene (mixture of m-chloromethylstyrene and p- chloromethylstyrene) was reacted with 0.1 mole of m-xylylene dimercaptan in the presence of 0.2 mole of sodium hydroxide in 200 ml of methanol as the solvent for 1 hour. After the reaction, the reaction product was washed with water. The reaction product obtained was liquid at room temperature, and from the results of the liquid chromatography, $H^1$-NMR and IR, it was confirmed that the product obtained was the following compound:

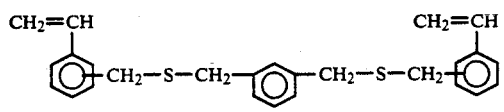

Some of the analytical data obtained are as follows.
NMR: 3.6 ppm (proton of methylene, 8H), 5.2–6.9 ppm (proton of vinyl group, 6H) and 7.1–7.4 ppm (proton of benzene nucleus, 12H)

(2) A mixture of 1 part by weight of benzoyl peroxide and 100 parts by weight of the monomer thus obtained was cast in a mold constructed by two glass sheets and silicone packings, and the temperature was elevated from 60° C. to 110° C. over a period of 12 hours to effect polymerization. The cured product obtained had a refractive index $\eta_D$ of 1.67, an Abbe number $\nu_D$ of 28 and a specific gravity d of 1.18.

EXAMPLE 2

By using a mixture (liquid) of 80 parts by weight of the monomer obtained in Example 1 and 20 parts by weight of p-bis($\beta$-methacryloyloxyethylthio)xylylene, polymerization was carried out in the same manner as described in Example 1. The cured product obtained had a refractive index $\eta_D$ of 1.65, an Abbe number $\nu_D$ of 29 and a specific gravity d of 1.20.

EXAMPLE 3

(1) At room temperature, 0.15 mole of m-xylylene dichloride was reacted with 0.25 mole of sodium sulfide in a 1/1 mixture of water and methanol as the solvent for 1 hour. Then, 0.2 mole of chloromethylstyrene (mixture of m-chloromethylstyrene and p-chloromethylstyrene) was added to the reaction mixture and reaction was further conducted at room temperature for 1 hour. After the reaction, the reaction product was washed with water. The reaction product obtained was liquid at room temperature. From the results of GPC, $H_1$-NMR and IR, it was confirmed that the reaction product was the following compound:

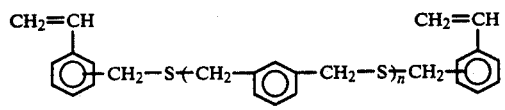

The product obtained was a mixture of compounds of the above formula in which n was 1 through 4 and the average value of n was 1.5.

Some of the analytical data obtained are as follows.
NMR: 3.6 ppm (proton of methylene, 10H), 5.2–6.9 ppm (proton of vinyl group, 6H) and 7.1–7.4 ppm (proton of benzene nucleus, 14H)

(2) By using a mixture (liquid) of 90 parts by weight of the monomer thus obtained and 10 parts by weight of methyl methacrylate, polymerization was carried out in the same manner as described in Example 1. The cured product obtained had a refractive index $\eta_D$ of 1.65, an Abbe number $\nu_D$ of 28 and a specific gravity d of 1.18.

COMPARATIVE EXAMPLE 1

(1) The experiment was carried out in the same manner as described in Example 1-(1) except that 0.1 mole of sodium sulfide was used instead of m-xylylene dimercaptan and sodium hydroxide. From the results of the liquid chromatography, $H^2$-NMR and IR, it was confirmed that the reaction product obtained was the following compound:

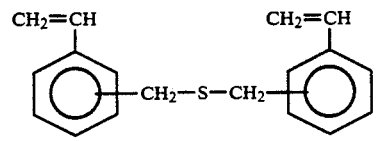

(2) Polymerization was carried out in the same manner as described in Example 1-(2). The cured product obtained was brittle and was broken when it was taken out from the glass mold. When the cured product was polished for measuring the refractive index, edges were broken off. The cured product had a refractive index $\eta_D$ of 1.65, an Abbe number $\nu_D$ of 28.

EXAMPLES 4 through 6

Compounds differing in the values of a, b and n were synthesized according to the process of Example 1 or Example 3. The physical property values of the obtained diethylenically unsaturated compounds were as shown below.

| Example No. | a,b | n | NMR |
|---|---|---|---|
| 4 | 0 | 1 | 3.6 ppm (proton of methylene, 4H) 5.2–6.9 ppm (proton of vinyl group, 6H) 7.1–7.5 ppm (proton of benzene nucleus, 12H) |
| 5 | 2 | 1 | 2.5–2.7 ppm (proton of ethylene chain, 8H) 3.6 ppm (proton of methylene, 4H) 5.2–6.9 ppm (proton of vinyl group, 6H) 7.1–7.4 ppm (proton of benzene nucleus, 12H) |
| 6 | 1 | 2.0 (average value) | 3.6 ppm (proton of methylene, 12H) 5.2–6.9 ppm (proton of vinyl group, 6H) 7.1–7.4 ppm (proton of benzene nucleus, 12H) |

What is claimed is:

1. An optical resin which is substantially insoluble and infusible and has a refractive index $\eta_D$ of at least 1.62, said resin comprising recurring units represented by the following formula [Ib]:

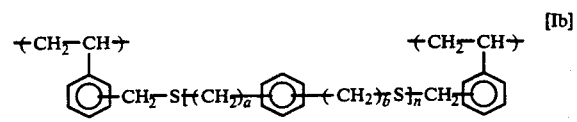

2. The optical resin as set forth in claim 1, wherein n is 1.

3. The optical resin as set forth in claim 1, wherein each of the phenylene groups in the formula is an m-phenylene or p-phenylene group.

4. The optical resin as set forth in claim 1, wherein the recurring units of formula (Ib) are derived from a diethylenically unsaturated monomer selected from the group consisting of:

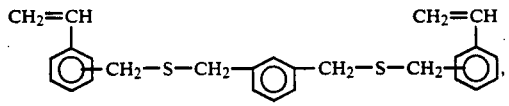

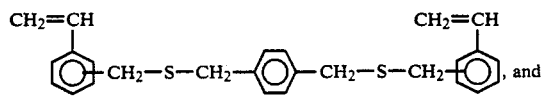, and

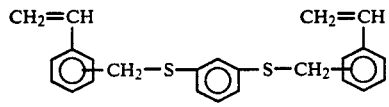

or mixtures of diethylenically unsaturated monomers each having the following formula:

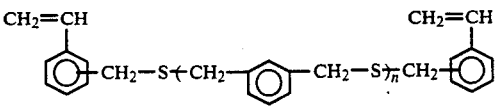

wherein n is 1 through 4, the average value being from more than 1 to 2.5.

5. The optical resin as set forth in claim 1, which is formed by radical polymerization of a monomer comprising at least 50% by weight of a diethylenically unsaturated monomer as set forth in claim 1 and up to 50% by weight of a monomer radically copolymerizable therewith.

6. The optical resin as set forth in claim 1, wherein at least a portion of recurring units of formula (Ib) in said optical resin have differing n values.

7. The optical resin as set forth in claim 6, wherein the n values of said recurring units having differing n values are 1 through 6.

* * * * *